United States Patent [19]

Steer

[11] Patent Number: 4,640,494
[45] Date of Patent: Feb. 3, 1987

[54] TAP OR VALVE

[75] Inventor: Peter L. Steer, Surrey, England

[73] Assignee: Craig Medical Products, Limited, Sussex, England

[21] Appl. No.: 747,203

[22] Filed: Jun. 21, 1985

[30] Foreign Application Priority Data

Jul. 6, 1984 [GB] United Kingdom ............... 8417347

[51] Int. Cl.⁴ ............................................. F16K 31/00
[52] U.S. Cl. .................................... 251/354; 251/342; 604/250; 285/260
[58] Field of Search ............... 604/34, 250; 251/342, 251/9, 4, 149.8; 285/9 R, 22, 260, DIG. 20, DIG. 24

[56] References Cited

U.S. PATENT DOCUMENTS

| 2,444,449 | 7/1948 | Kearny | 251/4 |
| 3,029,059 | 4/1962 | Hamilton et al. | 604/250 |
| 3,100,486 | 8/1963 | Nehring | 604/250 |
| 3,464,721 | 9/1969 | Surko, Jr. | 285/260 |
| 3,612,409 | 10/1971 | Henning | 285/260 |
| 3,977,409 | 8/1976 | Brendling | 251/342 |
| 4,063,706 | 12/1977 | Osborne, Jr. | 251/4 |

FOREIGN PATENT DOCUMENTS 890018 2/1962 United Kingdom ............... 251/4

Primary Examiner—A. Michael Chambers
Attorney, Agent, or Firm—Lawrence S. Levinson; Robert E. Lee, Jr.

[57] ABSTRACT

A tap or valve comprising a first tube and a second tube with a flexible elastic coupling between said tubes to allow fluid passage between said tubes when said tubes are substantially coaxially aligned and to allow displacement of one of said tubes relative to the other in order to close said fluid passage. The tap or valve is primarily intended for use with wire drawings tubing or intravenous drip tubing. The tap or valve further comprises means for releasably locking the tap or valve in the closed position.

6 Claims, 3 Drawing Figures

TAP OR VALVE

BACKGROUND OF THE INVENTION

This invention relates to a tap or valve. The tap or valve particularly described and illustrated herein is primarily intended for use with urine drainage tubing or intravenous drip tubing, but the present invention is not limited to these applications.

SUMMARY OF THE INVENTION

According to the present invention, there is provided a tap or valve comprising a first tube and a second tube with a flexible elastic coupling between said tubes to allow fluid passage between said tubes when said tubes are substantially coaxially aligned and to allow displacement of one of said tubes relative to the other in order to close said fluid passage.

The first and second tubes are conveniently constructed from rigid or semi-rigid plastics such as polyethylene. The flexible coupling between the tubes is conveniently formed by placing a sleeve of flexible elastic material, e.g., silicone rubber, over abutting or nearly abutting ends of the tubes. The flexible material should be impervious to the fluid to be passed through the tap and should provide a fluid seal at the outside walls of the tubes. The abutting ends of the tubes are conveniently provided with flanges or lips so that when the tubes are displaced to the closed position, the flanges engage to help to maintain the displaced tubes in this position. If desired, additional means may be provided to releasably lock the tap or valve in the closed position.

The tap or valve according to the invention may be cheaply and easily manufactured and can advantageously be used in a wide variety of applications.

An embodiment of the invention will now be described by way of example with reference to the accompanying drawings in which:

DETAILED DESCRIPTION OF THE DRAWINGS

Figure 1:
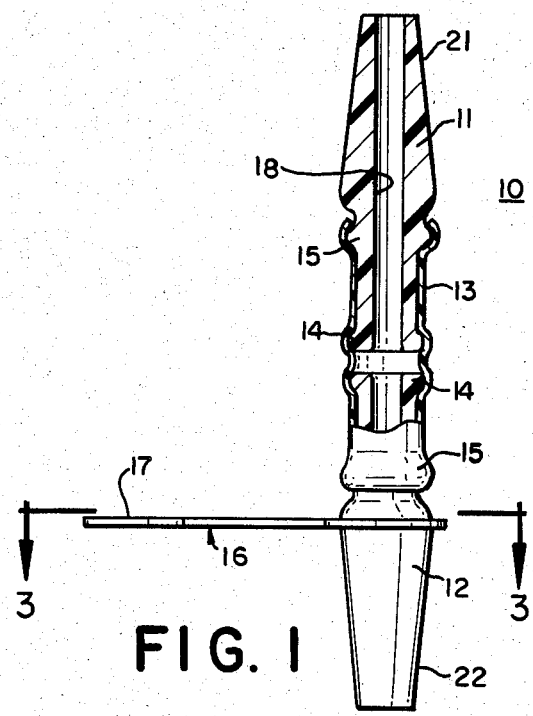
FIG. 1 shows a partial cross-section of a tap or valve according to the invention in an open position to allow fluid flow therethrough.
Figure 2:
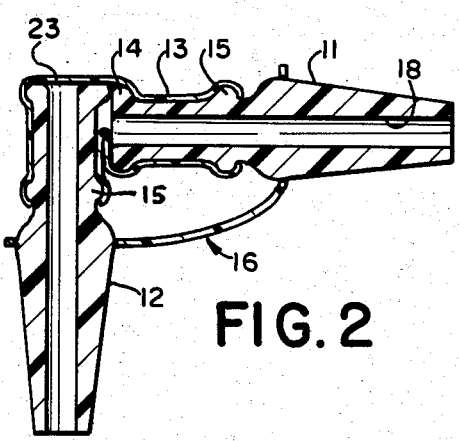
FIG. 2 shows a cross-section of the tap or valve according to FIG. 1 in a closed position.

Referring to FIGS. 1 and 2, a preferred embodiment tap or valve designated generally 10 is disclosed. It comprises two tubes 11 and 12 made from rigid plastics and are generally identical. The elongated ends 21 and 22 of the tubes 11 and 12, respectively opposite the coupling 13, have a tapering outside diameter for ease of connection to e.g. rubber or plastics tubing. If desired the elongated ends may be provided with one or more circumferential ribs to help to secure the tubes to the rubber or plastic tubing.

At their abutting or nearly abutting ends (facing ends), each tube is provided with a circumferential end flange 14, and a further flange 15 is provided intermediate the end flange 14 and the tapering end portions 21 and 22 of the tubes 11 or 12, respectively. The distance between the flanges 14 and 15 is generally similar to the outside diameter of the end flange 14.

The coupling 13 between the tubes 11 and 12 comprises a sleeve of flexible elastic material, e.g. silicone rubber. The coupling 13 generally provides a fluid tight coupling between the tubes 11 and 12, and in the position shown in FIG. 1 fluid is able to flow between tubes 11 and 12 through channel 18. The flanges 14 and 15 help to secure the flexible sleeve 13 to the tubes 11 and 12.

When it is desired to close the tap or valve shown in FIG. 1 the tubes 11 and 12 may be displaced relative to each other to the position shown in FIG. 2.

FIG. 2 shows the position of the tubes 11 and 12 when they are moved at right angles to their common axis as shown in FIG. 1. This may be achieved by holding one of the tubes, e.g. 12, and pushing the other, e.g. 11, at right angles to the common axis. Due to the arrangement of flanges 14 and 15, the pushed tube 11 will flick over with the end flange 14 of each tube engaging the other and with the flange 15 of the pushed tube engaging with or proceeding no farther than the end flange 15 of the tube 12. At the same time, the flexible elastic coupling material 13 will be stretched across the end 23 of the held tube 12 to close the tap or valve. The tap or valve can be simply reopened by pushing the tubes back to their original positions as shown in FIG. 1.

Figure 3:
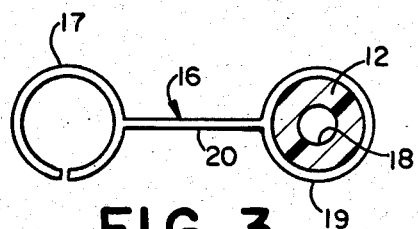
FIG. 3 is a cross-section of the tap or valve of FIG. 1 along the lines and arrows 3—3.

Optionally, the tap or valve is provided with means 16 in FIG. 3 for releasably locking the tubes in the closed position. In FIG. 3, the means 16 is preferably made of flexible plastic and comprises two loops 17 and 19 coupled together by a flexible connecting portion 20. Loop 19 is shown closed in position around the maximum diameter portion of tube 12 intermediate flange 15 of the tapered end portion 22 while loop 17 is open and adapted to be releasably clamped around tube 11. When the tubes 11 and 12 are in the closed position as shown in FIG. 2 and the open loop 17 is snapped into position around the body of tube 11, the means 16 acts to lock the tubes 11 and 12 in the closed positon. In order to open the tap or valve, i.e., return the tubes to the aligned position of FIG. 1, the loop 17 is removed from the body of tube 11. Closed loop 19 secured to tube 12 keeps the means 16 with the tap 10.

I claim:

1. A tap comprising a first tube, a second tube and a sleeve of flexible elastic material placed over abutting or nearly abutting ends of the tubes to form a flexible elastic coupling between said tubes to allow fluid passage between said tubes when said tubes are substantially coaxially aligned and to allow displacement of one of said tubes substantially at right angles to the other by stretching said sleeve across an open end of one of said tubes to close said fluid passage, the facing ends of the tubes each comprising at least one flange so that when the tubes are displaced to the closed position at substantially right angles to one another, the flanges engage to help to maintain the displaced tubes in the closed position.

2. The tap of claim 1 wherein the flexible elastic coupling is formed from silicone rubber.

3. The tap of claim 1 wherein each tube comprises at least two spaced apart flanges separated by a distance substantially equal to the outside diameter of the flange nearest the facing end.

4. The tap of claim 1 wherein said tap further comprises means for releasably locking the tap in the closed position.

5. The tap of claim 4 wherein said locking means comprises a flexible open loop portion for releasably coupling around one of said first or second tubes; and a flexible coupling member secured to said open loop and the remaining tube.

6. The tap of claim 1 wherein the first and second tubes are constructed from rigid or semi-rigid plastics.

* * * * *